(12) United States Patent
Holland

(10) Patent No.: US 6,517,562 B1
(45) Date of Patent: Feb. 11, 2003

(54) DEVICE FOR RELIEF OF ANAL PAIN

(76) Inventor: Graham M. Holland, 10 Burney Bit, Pamber Heath, Basingstoke, Hants RG26 3TN (GB)

(*) Notice: Subject to any disclaimer, the term of this patent is extended or adjusted under 35 U.S.C. 154(b) by 0 days.

(21) Appl. No.: 09/690,693

(22) Filed: Oct. 16, 2000

(30) Foreign Application Priority Data

Mar. 24, 2000 (GB) .............................................. 0007145

(51) Int. Cl.$^7$ ............................................. A61M 29/00
(52) U.S. Cl. ...................................................... 606/197
(58) Field of Search ................................. 606/191–195, 606/32, 41, 27, 1, 197; 607/98–102, 113

(56) References Cited

U.S. PATENT DOCUMENTS 3,667,465 A * 6/1972 Voss ............................ 606/191
4,341,211 A * 7/1982 Kline .......................... 606/191
5,860,806 A * 1/1999 Pranitis et al. ............. 206/63.5

* cited by examiner

Primary Examiner—Kevin T. Truong
(74) Attorney, Agent, or Firm—John Smith-Hill; Smith-Hill and Bedell

(57) ABSTRACT

A device for relief of anal pain includes a rod having first and second opposite end segments. The first end segment is shaped for grasping in the hand. There is a substantially annular flange structure between the first and second end segments, the flange structure having an external cylindrical surface. A cap has an interior surface which defines a cavity for receiving the second end segment of the rod, the interior surface of the cap being adapted to engage in sealing fashion the external cylindrical surface of the flange.

15 Claims, 1 Drawing Sheet

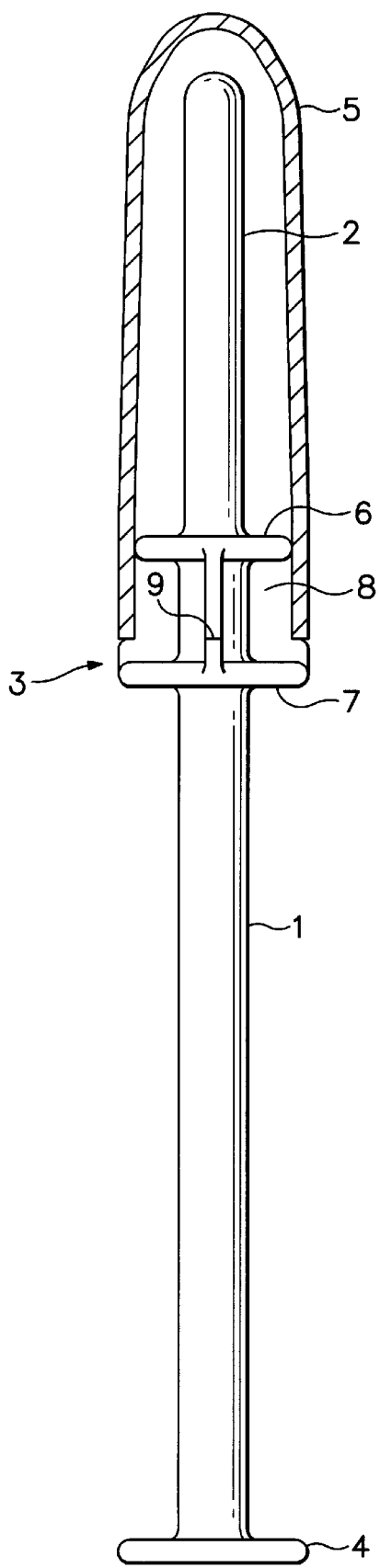

DEVICE FOR RELIEF OF ANAL PAIN

BACKGROUND OF THE INVENTION

This invention relates to a device for relief of pain. More specifically, it relates to a device for the relief of anal pain arising from hemorrhoids (piles) or other anal problems.

A number of devices have been provided in the art for relief of anal pain, but most of them are not suitable for contingent use by the sufferer himself, or are not able to provide relief inexpensively.

EP-A-0672400 describes a cooling cylindrical device for removal of pain and therapeutic treatment of hemorrhoids and anal fissures comprising a hollow insert, finger or bulb shaped for insertion into the anus with at least one inlet and/or outlet openings at its upper base, one or two tubes connected to these openings, and at least one container for cold liquid circulation starting from a container through an inlet tube into the cylindrical insert, the liquid being driven back through the outlet opening and through the second tube to the container, under the influence of a pump connected to the container or back to another container under the influence of gravity.

U.S. Pat. No. 4,331,151 describes a hemorrhoid bandage or cold pack, for positioning within a human anal canal, formed of a hollow, thin wall, roughly cylindrically shaped body having an inner end and an outer end. The body is transversely divided into two parts by a central panel extending longitudinally from the outer end towards the inner end, but having an open area adjacent the inner end. A tube, which is coaxial with the body, extends from the inner to the outer end and opens exteriorly of the body at each end. A fluid inlet continuously supplies fluid into one body part through the outer end, which fluid flows through the panel open area at the inner end, and then out of the other body part through a fluid drain opening communicating therewith. The two interior parts may be further subdivided by transverse ribs extending between the panel and the body exterior wall to form longitudinally extending channels for controlling the direction of the fluid flow through the body. By using a relatively cool fluid, such as cool water, the bandage may be used to provide a controlled temperature, for extended periods of time, within the rectal area in connection with treatment of hemorrhoids.

U.S. Pat. No. 4,563,182 describes a method of treating hemorrhoids which comprises inserting into the rectum of a subject afflicted therewith a substantially cylindrical shaped insert, comprising a water swellable polymer having a water content of at least 35% by weight, the insert having previously been subjected to a temperature below 0° C. for a sufficient amount of time to freeze the free water therein, and maintaining the insert with at least a portion thereof outside the sphincter muscle.

U.S. Pat. No. 4,841,970 describes a cryogenic proctologic insert for treating hemorrhoids by lowering the surface temperature of the affected portion of the rectal canal. The insert is formed of a tubular plastic portion filled with a congealable fluid. Extended heat transfer surfaces are provided in the interior of the insert to promote heat transfer to and from the fluid.

U.S. Pat. No. 4,537,194 relates to an applicator used to apply a frozen solid such as ice to a wound or injury to treat the wound or injury. A first container has an open top of a predetermined size, a tapered side wall and a bottom having a central opening therethrough, and a second container has a shape conforming at least in part to that of the first container, an open top and a closed bottom. The two containers are fitted together by placing the bottom of the first container into the top of the second container. The device can then be filled with liquid and frozen until needed. When in use as an applicator, the second container is removed and the first container serves as a handle for applying the frozen solid.

DE-A-3802218 relates to a method and a device for producing ice for medical treatment, especially for therapeutic massage, in which water filled in a container is subjected to a freezing process. During the freezing process the water present in the container is molded onto a carrier element as a compact body of ice which is uncovered during the medical treatment.

Other devices are known of greater or lesser complication and practicality. There still remains the need, however, for a simple and inexpensive means of providing relief for anal pain.

SUMMARY OF THE INVENTION

In accordance with the present invention there is provided a device for relief of anal pain comprising a rod having first and second opposite end segments, the first end segment being shaped for grasping in the hand, a substantially annular flange structure between the first and second end segments, the flange structure having an external cylindrical surface, and a cap having an interior surface defining a cavity for receiving the second end segment of the rod, the interior surface of the cap being adapted to engage in sealing fashion the external cylindrical surface of the flange.

BRIEF DESCRIPTION OF THE DRAWINGS

For a better understanding of the invention, and to show how the same may be carried into effect, reference will now be made, by way of example, to the accompanying drawings, the single FIGURE of which is a partial sectional view of a device in accordance with the invention.

DETAILED DESCRIPTION

Referring now to the drawings, the device according to the invention comprises a rod having first and second opposite ends segments 1 and 2 extending to opposite respective sides of a flange structure 3. The end segment 1 is adapted to be grasped in the hand. At the free end of this segment, the rod is optionally provided with an enlarged portion 4 for convenient holding in the hand. The enlarged portion 4 is shown as having a shape that is substantially a disc, but other shapes can be employed.

The flange structure 3 includes a smaller diameter annular flange 6, a larger diameter annular flange 7, and four linear webs 8 extending between the flanges 6 and 7. The webs 8 are each formed with a step to provide a transition from the smaller diameter of the flange 6 to the larger diameter of the flange 7.

A cap 5 fits over the second end segment 2 of the rod. The cap 5 fits over the end segment 2 with a push fit, so as to form a seal with the smaller flange 6. Nevertheless, the cap can be easily removable by simple pulling. The rim of the cap 5 engages the step 9, which ensures a clearance between the rim of the cap and the larger flange 7.

The dimensions of the device according to the invention are not critical, subject to the overriding factor that they must not be too small or too large for the device to fulfill its intended function.

Typically the rod may have an overall length of from 110 to 130 mm, preferably about 120 mm. The first end segment 1 may have a length from 75 to 85 mm, preferably 80 mm, and a diameter from 4 to 6 mm, preferably 5 mm. The second end segment 2 may have a length from 30 to 40 mm, preferably about 35 mm, and the diameter of the end segment 2 may be from 3.5 to 4.5 mm, preferably 4 mm. The enlarged portion 4 and the larger flange 7 each may have a thickness of 1.5 to 2.5 mm, preferably 2 mm, and diameter from 12 to 16 mm, preferably 14 mm. The smaller flange 6 may have a thickness of 1.5 to 2.5 mm, preferably 2 mm, and a diameter from 11.5 to 13.5 mm, preferably 12.5 mm. The cap 5 may have a length of 40 to 60 mm, preferably 50 mm and an external diameter of 13 to 17 mm, preferably 15 mm.

To prepare for use, the cap 5 is filled with water, optionally containing a disinfectant or analgesic material, and the end segment 2 is inserted fully in the cap so that the smaller flange 6 enters the cap and the step 9 abuts the rim of the cap. The interior surface of the cap seals against the exterior of the smaller flange so that the water is retained in the cap. The device is then placed in a freezer for a sufficient time for the water to freeze. Expansion of the water when it freezes is accommodated by the sliding fit of the cap 5 on the smaller flange 6. For use, the cap is removed from the rod and a body of ice substantially in the form of a cylinder or tapered cylinder, with an end again forming a slightly rounded conical portion, is held firmly on the end segment 2. The user can then grip the device by the end segment 1, with the aid of the enlarged portion 4, and insert the ice body into the anus for the contingent relief of pain.

The webs 8 ensure that the end segment 2 is aligned with the central axis of the cap when the cap is fitted on the end segment 2. The step 9 provided on the webs 8 limits the depth to which the end segment 2 can enter the cap and therefore ensures that the tip of the end segment is covered by the end of the ice body.

It will be appreciated that the invention is not restricted to the particular embodiment that has been described, and that variations may be made therein without departing from the scope of the invention as defined in the appended claims and equivalents thereof. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated.

What is claimed is:

1. A device for relief of anal pain comprising:
   an elongate rod having first and second opposite end segments, the first end segment being shaped for grasping in the hand and the second end segment having a tip,
   a substantially annular flange structure between the first and second end segments, the flange structure having an external cylindrical surface, and
   a cap having an interior surface defining a cavity for receiving the second end segment of the rod, the interior surface of the cap being adapted to engage in sealing fashion the external cylindrical surface of the flange and being of substantially uniform cross-section over substantially the entire length of the rod from the flange structure to the tip of the second end segment.

2. A device according to claim 1, wherein the cap has a rim and the flange structure includes a shoulder which is abutted by the rim of the cap when the cap is fitted over the second end segment of the rod to limit penetration of the second end segment into the interior of the cap.

3. A device according to claim 1, wherein the flange structure includes an annular flange having an external peripheral surface that constitutes said external cylindrical surface.

4. A device according to claim 1, wherein the flange structure includes a smaller annular flange, a larger annular flange spaced from the smaller annular flange, and a plurality of linear webs connecting the smaller and larger flanges, and wherein the smaller annular flange is between the larger annular flange and the second end segment of the rod and the smaller annular flange has an external peripheral surface that constitutes said external cylindrical surface.

5. A device according to claim 4, wherein the webs include a step between the smaller annular flange and the larger annular flange and the step is abutted by the rim of the cap when the cap is fitted over the second end segment of the rod to limit penetration of the second end segment into the interior of the cap.

6. A device for relief of anal pain comprising:
   an elongate rod having first and second opposite end segments, the first end segment being shaped for grasping in the hand and the second end segment having a tip,
   a substantially annular flange structure between the first and second end segments, the flange structure having an external surface, and
   an elongate cap having first and second opposite ends, the cap being open at its first end and closed at its second end and having an interior surface defining a cavity for receiving the second end segment of the rod by way of the first end of the cap, the interior surface of the cap being adapted to engage in sealing fashion the external surface of the flange and being of substantially uniform cross-section over substantially the entire length of the rod from the flange structure to the tip of the second end segment.

7. A device according to claim 6, wherein the cap has a rim at the first end and the flange structure includes a shoulder which is abutted by the rim of the cap when the cap is fitted over the second end segment of the rod to limit positively penetration of the second end segment into the interior of the cap.

8. A device according to claim 6, wherein the flange structure includes an annular flange having an external peripheral surface that constitutes said external surface.

9. A device according to claim 6, wherein the flange structure includes a smaller annular flange, a larger annular flange spaced from the smaller annular flange, and a plurality of linear webs connecting the smaller and larger flanges, and wherein the smaller annular flange is between the larger annular flange and the second end segment of the rod and the smaller annular flange has an external peripheral surface that constitutes said external surface.

10. A device according to claim 9, wherein the webs include a step between the smaller annular flange and the larger annular flange and the step is abutted by the rim of the cap when the cap is fitted over the second end segment of the rod to limit penetration of the second end segment into the interior of the cap.

11. A device for relief of anal pain comprising:
    an elongate rod having first and second opposite end segments, the first end segment being shaped for grasping in the hand, a substantially annular flange structure between the first and second end segments, the flange structure having all external surface, and an elongate cap having first and second opposite ends, the cap having an opening at its first end and being closed at its second end and having an interior surface defining a cavity, wherein the second end segment of the rod is located in the cavity and the first end segment projects from the cavity by way of the opening at the first end of the cap, the interior surface of the cap engages the external surface of the flange in sealing fashion, and the interior surface of the cap is spaced from the rod over the entire length of the second end segment of the rod.

12. A device according to claim 11, wherein the cap has a rim at the first end and the flange structure includes a shoulder which is abutted by the rim of the cap to limit positively penetration of the second end segment into the interior of the cap.

13. A device according to claim 11, wherein the flange structure includes an annular flange having an external peripheral surface that constitutes amid external surface.

14. A device according to claim 11, wherein the flange structure includes a smaller annular flange, a larger annular flange spaced from the smaller annular flange, and a plurality of linear webs connecting the smaller and larger flanges, and wherein the smaller annular flange is between the larger annular flange and the second end segment of the rod and the smaller annular flange has an external peripheral surface that constitutes said external surface.

15. A device according to claim 14, wherein the webs include a step between the smaller annular flange and the larger annular flange and the step is abutted by the rim of the cap to limit penetration of the second end segment into the interior of the cap.

* * * * *